US008580347B2

(12) United States Patent
Koike et al.

(10) Patent No.: US 8,580,347 B2
(45) Date of Patent: Nov. 12, 2013

(54) METHOD FOR PRODUCING CALCIUM PHOSPHATE COMPLEX

(75) Inventors: Kunihiko Koike, Moriyama (JP); Masami Nakagawa, Moriyama (JP); Tsutomu Furuzono, Minoo (JP)

(73) Assignees: Iwatani Corporation, Osaka (JP); National Cerebral and Cardiovascular Center, Osaka (JP)

( * ) Notice: Subject to any disclaimer, the term of this patent is extended or adjusted under 35 U.S.C. 154(b) by 228 days.

(21) Appl. No.: 12/734,358

(22) PCT Filed: Oct. 23, 2008

(86) PCT No.: PCT/JP2008/069219
§ 371 (c)(1),
(2), (4) Date: Apr. 27, 2010

(87) PCT Pub. No.: WO2009/057502
PCT Pub. Date: May 7, 2009

(65) Prior Publication Data
US 2010/0247736 A1 Sep. 30, 2010

(30) Foreign Application Priority Data
Nov. 1, 2007 (JP) ................................. 2007-285272

(51) Int. Cl.
*B05D 1/18* (2006.01)

(52) U.S. Cl.
USPC .......................... 427/323; 427/299; 427/430.1

(58) Field of Classification Search
USPC ...................................................... 427/430.1
See application file for complete search history.

(56) References Cited

U.S. PATENT DOCUMENTS

| 5,378,768 A | 1/1995 | Ogisu et al. .................... 525/388 |
| 6,387,414 B1 | 5/2002 | Akashi et al. | |
| 7,767,220 B2 | 8/2010 | Ranade et al. ................. 424/423 |
| 2002/0127262 A1* | 9/2002 | Akashi et al. ................. 424/423 |
| 2004/0236432 A1* | 11/2004 | Hyon et al. .................. 623/23.51 |
| 2005/0119732 A1* | 6/2005 | Furuzono et al. ............. 623/1.49 |

FOREIGN PATENT DOCUMENTS

| JP | 06-248103 | | 9/1994 |
| JP | 06293504 A | * | 10/1994 |
| JP | 08-109228 | | 4/1996 |
| JP | 08215618 A | * | 8/1996 |
| JP | 2000-290405 | | 10/2000 |
| JP | 2000290405 A | * | 10/2000 |
| JP | 2001-348445 | | 12/2001 |
| JP | 2004-017410 | | 1/2004 |
| JP | 2005-093989 | | 4/2005 |
| JP | 2005-146120 | | 6/2005 |
| JP | 2007-533408 | | 11/2007 |

OTHER PUBLICATIONS

T. Furuzono, et al., "Nano-scaled hydroxyapatite/polymer composite IV. Fabrication and cell adhesion properties of a three-dimensional scaffold made of composite material with a silk fibroin substrate to develop a percutaneous device" J. Artif. Organs, 7 p. 137-144 (2004).

* cited by examiner

*Primary Examiner* — David Turocy
(74) *Attorney, Agent, or Firm* — Harness, Dickey & Pierce, P.L.C.

(57) ABSTRACT

A method of the present invention for producing a calcium phosphate complex including a substrate and calcium phosphate bonded to a surface of the substrate, the method includes the steps of: (a) treating the surface of the substrate; and (b) bonding the calcium phosphate onto the surface of the substrate after the step (a), the step (a) being the step of placing the surface of the substrate in contact with ozone water. Therefore, the method of the present invention makes it possible to bond calcium phosphate and the substrate at a high bonding strength and at a high coverage. In addition, the method of the present invention provides an easy method for producing a calcium phosphate complex.

4 Claims, 13 Drawing Sheets

FIG. 8
(a)
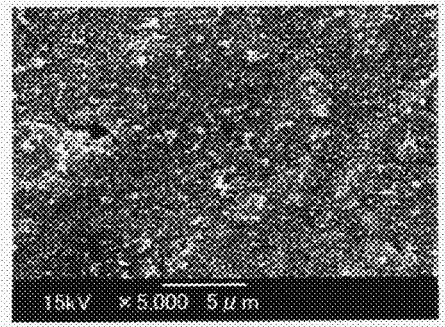
(b)
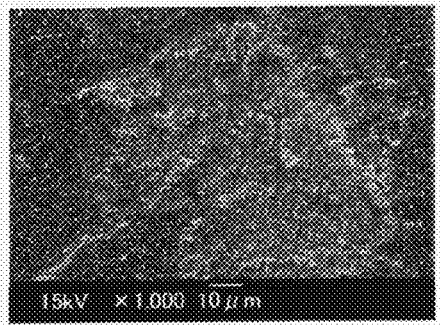
(a')
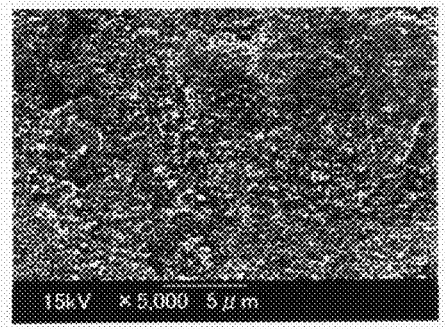
(b')
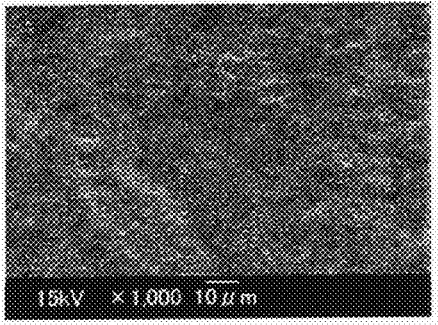

METHOD FOR PRODUCING CALCIUM PHOSPHATE COMPLEX

TECHNICAL FIELD

The present invention relates to a method for producing a calcium phosphate complex. More specifically, the present invention relates to a method for producing a calcium phosphate complex including a substrate and calcium phosphate bonded to the substrate at a high bonding strength and at a high coverage by performing ozone water treatment.

BACKGROUND ART

Calcium phosphate such as hydroxyapatite is widely used as a biocompatible material in a medical field.

It is expected that, in particular, a complex material prepared by coating a surface of a substrate with calcium phosphate is applied to a percutaneous device such as a catheter, because such a complex material has a high cell adhesion. For example, there has been proposed a technique to use, for a percutaneous device, a complex material prepared by bonding fine particles of calcium phosphate to a surface of a flexible polymer substrate made of, for example, silk fibroin (e.g. Patent Literatures 1 and 2).

Patent Literatures 1 and 2 disclose, as a method for coating a surface of a substrate with calcium phosphate, a method for bonding calcium phosphate particles to the surface of the substrate by giving a functional group to the surface of the substrate. More specifically, after a surface of silk fibroin is treated first with a radical initiator such as hydrogen peroxide solution or ammonium persulfate (APS), a silane coupling agent is graft-polymerized onto the surface of the substrate. Thereby, the functional group is introduced onto the substrate. Then, the functional group and calcium phosphate are bonded and thereby, the substrate is coated with calcium phosphate.

Patent Literature 3 discloses a method for fixing hydroxyapatite on a surface of a substrate by immersing, into calcium solution, the substrate having been surface-treated by corona discharge treatment and plasma treatment. Apart from a purpose of bonding calcium phosphate, ozone treatment, ultraviolet irradiation, or the like is known as a method for treating a surface of a substrate (e.g. Patent Literatures 4 to 6)

CITATION LIST

Patent Literature 1

Japanese Patent Application Publication, Tokukai, No. 2004-51952 A (Publication Date: Apr. 19, 2004)

Patent Literature 2

Japanese Patent Application Publication, Tokukai, No. 2000-327314 A (Publication Date: Nov. 28, 2000)

Patent Literature 3

Japanese Patent Application Publication, Tokukai, No. 2005-146120 A (Publication Date: Jun. 9, 2005)

Patent Literature 4

Japanese Patent Application Publication, Tokukai, No. 2000-290405 A (Publication Date: Oct. 17, 2000)

Patent Literature 5

Japanese Patent Application Publication, Tokukai, No. 2005-93989 A (Publication Date: Apr. 7, 2005)

Patent Literature 6

Japanese Patent Application Publication, Tokukaihei, No. 8-109228 A (Publication Date: Apr. 30, 1996)

SUMMARY OF INVENTION

As described above, usability of a complex material including a substrate and calcium phosphate coating the substrate is strongly expected in a medical field.

In view of the above situation, it is required to have a technique to more easily bond the substrate and calcium phosphate at a high bonding strength and at a high coverage as compared with techniques as disclosed in Patent Literatures 1 through 3.

Accordingly, an object of the present invention is to provide an easy method for producing a calcium phosphate complex by which the substrate and calcium phosphate are bonded at a high bonding strength and at a high coverage.

In order to achieve the above object, inventors of the present invention made a diligent study and found that the substrate and calcium phosphate are bonded at a very high bonding strength and at a high coverage by treating a surface of the substrate with use of ozone water. Because ozone water is very easily handled and use of ozone water makes surface treatment efficient even in a case where the substrate has a complicated shape, the use of ozone water is a sufficient solution to achieve the above object. The present invention is achieved based on the novel finding described above and encompasses the inventions described below.

That is, in order to achieve the problem mentioned above, a method of the present invention for producing a calcium phosphate complex including a substrate and calcium phosphate bonded to a surface of the substrate, the method includes the steps of: (a) treating the surface of the substrate; and (b) bonding the calcium phosphate onto the surface of the substrate after the step (a), the step (a) being the step of placing the surface of the substrate in contact with ozone water.

Further, according to the method of the present invention, an ozone concentration of the ozone water is preferably in a range of 1 ppm or more to 50 ppm or less.

Further, according to the method of the present invention, a time for keeping the surface of the substrate in contact with the ozone water is in a range of 5 minutes or more to 30 minutes or less.

Further, according to the method of the present invention, the surface of the substrate is placed in contact with the ozone water at a temperature in a range of 20° C. or more to 60° C. or less.

Further, according to the method of the present invention, the substrate may be polyester, silk, silicone, polystyrene, polyurethane, or polymethylmethacrylate.

For a fuller understanding of the nature and advantages of the invention, reference should be made to the ensuing detailed description taken in conjunction with the accompanying drawings.

BRIEF DESCRIPTION OF DRAWINGS

FIG. 8 is a diagram illustrating results of observation of a Hap complex before and after ultrasonic probe treatment in Example 9; (a) and (b) of FIG. 8 show a result of observation of the Hap complex before the ultrasonic probe treatment and (a') and (b') of FIG. 8 show a result of observation of the Hap complex after the ultrasonic probe treatment.

DESCRIPTION OF EMBODIMENTS

Figure 1:
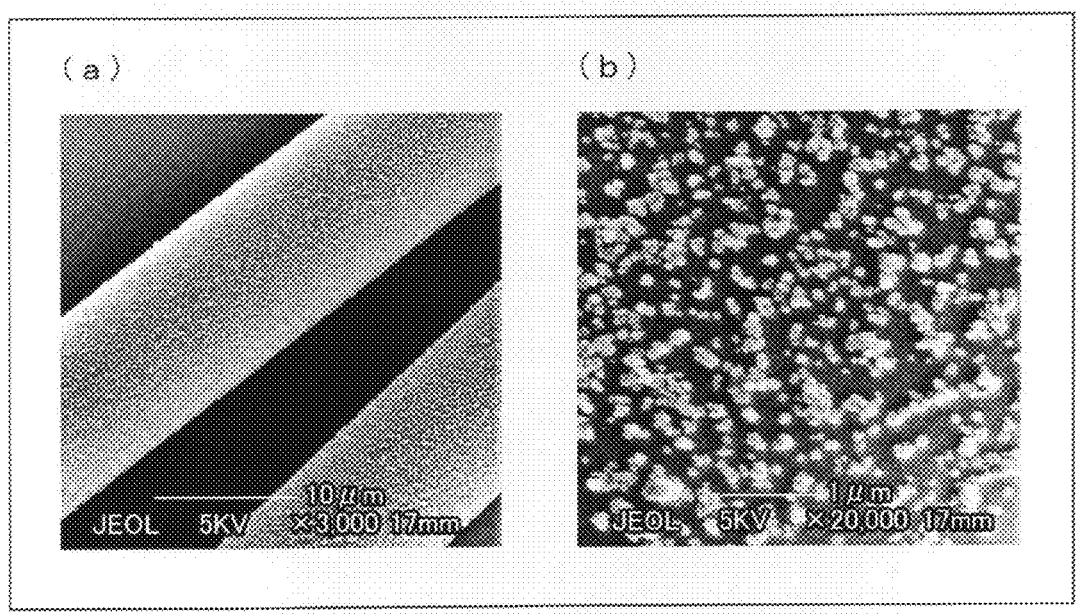
FIG. 1 is a diagram illustrating results of observing, by use of a scanning electron microscope, a Hap complex obtained in Example 1; (a) of FIG. 1 shows a result of observation at 3,000 times magnification and (b) of FIG. 1 shows a result of observation at 20,000 times magnification.

The following describes one embodiment of the present invention.

A method for producing a calcium phosphate complex (hereinafter, simply referred to as a "production method of the present invention" or "method of the present invention") may include: (a) surface treatment step for treating the surface of the substrate; and (b) bonding step for bonding the calcium phosphate onto the surface of the substrate after the step (a), the step (a) being the step of placing the surface of the substrate in contact with ozone water.

In the present specification, the "calcium phosphate complex" means a structure obtained by bonding calcium phosphate to a surface of a substrate. In the present specification, the "ozone water" means water in which ozone is dissolved.

Further, in the present specification, the "surface treatment" means a treatment for modifying the surface of the substrate. In an exemplary surface treatment, the surface of the substrate is brought into contact with ozone water so that a radical is formed on the surface of the substrate.

[Substrate]

The substrate in the production method of the present invention may be selected from various substrates. Examples of such substrates are: polymer substrates each including a polymeric material and inorganic substrates each including an inorganic material. More specifically, the polymer substrates may be, for example: synthetic polymers such as polyester (e.g. polyethylene telephthalate (hereinafter, referred to as "PET")), a silicone polymer (or silicone rubber), polyethyleneglycol, polyalkyleneglycol, polyglycolic acid, polylactic acid, polyamide, polyurethane, polysulfone, polyether, polyether ketone, polyamine, polyurea, polyimide, polyethylene, polypropylene, polytetrafluoroethylene, polyacrylic acid, polymethacrylic acid, polymethylmethacrylate, polyacrylonitrile, polystyrene, polyvinyl alcohol, and polyvinylchloride; and natural polymers such as polysaccharide (e.g.

cellulose, amylose, amylopectin, chitin, and chitosan), polypeptide (e.g. collagen), mucopolysaccharide (e.g. hyaluronic acid, chondroitin, chondroitin sulfate), and silk fibroin. However, the polymer substrate is not limited to the above described substrates. Among the above described substrates, polyester, silk fibroin, a silicone polymer, polylactic acid, and polyurethane, in particular, PET and silk fibroin are preferably used because these substrates are preferable as a medical material. Meanwhile, specific examples of the inorganic substrates are: titanium, titanium oxide, and stainless steel. It is one of advantageous effects of the production method of the present invention that the substrate may be selected from among such various substrates, as described above. Though substrates that can be selected are limited according to a conventional method, the present inventions makes it possible to bond calcium phosphate to any of various substrates by performing ozone water treatment.

A shape of the substrate applicable to the present invention is not specifically limited. In accordance with an application of a calcium phosphate complex to be produced, the substrate may be selected from variously shaped substrates. For example, the substrate may be in the form of a fiber, a sheet, a tube, or a porous body or may have a more complicated shape.

In this way, it is one of prominent effects of the present invention that a Hap complex can be easily produced regardless of a shape of the substrate, even by using a substrate of a complicated shape. According to a conventional method using corona discharge and/or plasma treatment, it is necessary to work out a method according to which, for example, corona discharge is carried out at various angles in the case of a substrate that has a complicated shape. However, according to the production method of the present invention, because the substrate only needs to be brought into contact with ozone water as described later, the surface treatment can be easily performed even on a substrate that has a complicated shape. In this way, the production method of the present invention makes it possible to easily bond calcium phosphate and a substrate of any of various shapes at a high bonding strength and at a high coverage.

[Calcium Phosphate]

Calcium phosphate used in the production method of the present invention is not specifically limited. However, as the calcium phosphate, hydroxyapatite ($Ca_{10}(PO_4)_6(OH)_2$) is preferable and a hydroxyapatite sintered body (also called hydroxyapatite ceramics) is more preferable. Because hydroxyapatite, in particular, the hydroxyapatite sintered body stays stable in a living body for a long term and has a high safety, hydroxyapatite is excellent as a material of a calcium phosphate complex for medical use. Further, because hydroxyapatite has a high adhesion to cells of, for example, skin, hydroxyapatite is excellent particularly as a material for a percutaneous device.

It should be noted that a method for producing the hydroxyapatite sintered body is not specifically limited but may be a conventionally known method. Patent Documents 1 and 2 may be referred to for, for example, the method for producing the hydroxyapatite sintered body and for measurement of crystallinity of the hydroxyapatite sintered body that has been produced.

[Surface Treatment Step]

A surface treatment step in the method of the present invention is the step of treating a surface of the substrate. The surface treatment step should be the step of placing the surface of the substrate into contact with ozone water.

Inventors of the present invention have found that, by treating a surface of a substrate by use of ozone water, calcium phosphate can be very easily bonded to the substrate. For example, even in a case where the substrate has a complicated shape, the substrate can be easily brought into contact with ozone water all over the surface of the substrate only by immersing the substrate into ozone water or by pouring ozone water onto the substrate. Therefore, a process can be carried out easily at a high efficiency.

Further, the inventors of the present invention have also found that calcium phosphate and the substrate can be bonded at a high bonding strength and at a high coverage by treating a surface of a substrate by use of ozone water. Conventionally, when a substrate coated with calcium phosphate was subjected to ultrasonic cleaning, calcium phosphate was peeled off in some cases. This is because of a weak bonding strength between calcium phosphate and the substrate. However, when calcium phosphate was bonded to the substrate whose surface had been treated by use of ozone water, peel-off of calcium phosphate could be prevented. Furthermore, in a case where a calcium phosphate complex is for medical use, a preferable coverage of calcium phosphate on the surface of the substrate is approximately 60%. However, conventionally, PET that was preferably used as a substrate for medical use could not be coated with calcium phosphate at the coverage of 60%. On the contrary, according to the present invention, by treating the surface of the substrate by use of ozone water, it is possible to coat PET with calcium phosphate uniformly at the coverage of 60%. Further, by treating the surface of the substrate by use of ozone water, various substrates other than PET can be coated with calcium phosphate uniformly at a high coverage.

It is considered that such an excellent bonding strength and an excellent coverage are realized because ozone water can introduce a radical to any substrate. For example, ozone water can favorably introduce a radical to a substrate even when the substrate such as PET has a surface terminated by an oxygen group or even when the substrate such as silk fibroin has a hydroxyl group on the surface.

Conventionally, it was difficult to introduce a radical efficiently to a substrate whose surface is terminated by an oxygen group. However, the inventors of the present invention have found that a radical can be introduced efficiently to an oxygen group by using ozone water.

In other words, according to a conventional technique, a substrate to which a radical could be introduced was limited. This limited a range of choice of materials that could be a substrate of a calcium phosphate complex. However, according to the present invention, the substrate can be selected from among variety of materials. This wide range of materials that can be selected as the substrate is a significantly superior point of the present invention to a conventional technique.

The present invention is attained based on such a completely novel finding that the inventors of the present invention have found.

Further, the present invention is superior to a method that employs a radical initiator such as APS, in the following point. That is, when a radical initiator is used in a case where silane coupling agent described later are used, a homopolymer as a result of polymerization of the silane coupling agents may become a contaminant. However, ozone water does not cause such a concern. Therefore, the present invention is superior in that a cleaning step and waste water treatment after bonding of calcium phosphate is simplified. In addition, there is a substance whose risk of explosion is pointed out among radical initiators and therefore handling of a radical initiator may become cumbersome. However, because ozone water has no risk of explosion, ozone water is easily handled and has a high safety. Therefore, the present invention is superior in view of easiness and safety.

Ozone water to be used in the step of treating the surface is not specifically limited as long as the ozone water is water in which ozone is dissolved. The ozone water may be produced by using a conventionally known method and a conventionally known device. For example, by aeration of ozone in water, the ozone water may be produced. As an apparatus for dissolving ozone into water, for example, a conventionally known stirrer, bubble tube, pressure type injector, venturi type injector, or static mixer may be used. For a method for producing the ozone water, Ozone Handbook edited by Nonprofit Organization Japan Ozone Association (Hidetoshi, Sugimitsu, Fundamentals and Applications of Ozone, Korin Publishing Co. Ltd.) may be suitably referred to.

An ozone concentration ozone water in the production method of the present invention is not specifically limited; however, the ozone concentration is preferably in a range of 1 ppm or more to 50 ppm or less, and more preferably in a range of 10 ppm or more to 35 ppm or less. When the ozone concentration of ozone water is arranged to be in a range of 1 ppm or more to 50 ppm or less, calcium phosphate can be bonded to the surface of the substrate at a very high bonding strength and at a high coverage. Further, when the ozone concentration of ozone water is arranged to be in a range of 10 ppm or more to 35 ppm or less, calcium phosphate can be bonded to the surface of the substrate at a higher bonding strength and at a higher coverage.

A temperature of ozone water is not specifically limited. However, the temperature is preferably in a range of 20° C. or more to 60° C. or less, more preferably in a range of 20° C. or more to 40° C. or less, and most preferably a room temperature (e.g. 25° C.). In this range, calcium phosphate can be bonded to the surface of the substrate at a very high bonding strength and at a high coverage.

A time for which the surface of the substrate is kept in contact with ozone water is not specifically limited. However, the time is preferably in a range of 5 minutes or more to 30 minutes or less, and more preferably in a range of 5 minutes or more to 20 minutes or less. In this range, calcium phosphate can be bonded to the surface of the substrate at a very high bonding strength and at a high coverage.

Further, a method for placing the surface of the substrate into contact with ozone water is not specifically limited. For example, the substrate may be immersed in ozone water. Further, during the immersion, the ozone water may be stirred.

[Bonding Step]

The bonding step in the production method of the present invention should be the step of bonding the calcium phosphate to the surface of the substrate after the surface treatment step.

A method for bonding calcium phosphate to the surface of the substrate after the surface treatment step is not specifically limited but may be a conventionally known method.

For example, calcium phosphate may be bonded to a substrate to which a functional group has been introduced by performing the step of introducing a functional group that makes it easy to bond calcium phosphate to the surface of the substrate. The following explains such a method, but the present invention is not limited to this method. For the method described below, Patent Literatures 1 and 2 may be referred to.

Suitable examples of such a functional group are an alkoxysilyl group and an isocyanate group. However, the functional group is not limited to these examples.

A method for introducing the alkoxysilyl group and/or the isocyanate group to the surface of the substrate is not specifically limited, but it is preferable to use a silane coupling agent. The silane coupling agent is a compound that includes, within a molecule, a part that is reactive to an inorganic substance and a part that is highly reactive and highly soluble with respect to an organic substance. Such a compound is used as a crosslinking agent for a boundary between an inorganic substance and an organic substance. When the step of introducing a functional group is performed by using a silane coupling agent after the surface treatment step, the silane coupling agent is graft-polymerized onto the surface of the substrate. Thereby, an alkoxysilyl group or the like included in the silane coupling agent is present on the surface of the substrate. Therefore, a bonding strength of calcium phosphate is improved. This means that, in regard to bonding between the silane coupling agent and the substrate whose surface has been treated by use of ozone water, a bonding strength is favorable. In other words, the surface treatment of the substrate by use of ozone water is excellent in improving a bonding strength of the silane coupling agent to the substrate. Though a method employing a silane coupling agent is disclosed also in Patent Literatures 1 and 2, it should be noted that an amount of a silane coupling agent used can be reduced in the present invention as compared to techniques disclosed in Patent Literatures 1 and 2. This is because, in the present invention, ozone water is used and the silane coupling agent can be graft-polymerized at a high efficiency.

In the production method of the present invention, the silane coupling agent that can be used is not specifically limited but may be a conventionally known silane coupling agent. Examples of the silane coupling agent are: a vinyl silane coupling agent such as vinyltrichlorosilane, vinyltrimethoxysilane and vinyltriethoxysilane; an epoxy silane coupling agent such as β-(3,4 epoxycyclohexyl)ethyltrimethoxysilane, γ-glycidoxypropyltrimethoxysilane, γ-glycidoxypropylmethyldiethoxysilane, and γ-glycidoxypropyltriethoxysilane; a styryl silane coupling agent such as p-styryltrimethoxysilane; a methacryloxy silane coupling agent such as methacryloxypropylmethyldimethoxysilane, γ-methacryloxypropyltrimethoxysilane, γ-methacryloxypropylmethyldiethoxysilane, and γ-methacryloxypropyltriethoxysilane; an acryloxy silane coupling agent such as γ-acryloxypropyltrimethoxysilane; an amino silane coupling agent such as N-β(aminoethyl)γ-aminopropyltrimethoxysilane, N-β(aminoethyl)γ-aminopropylmethyldimethoxysilane, N-β(aminoethyl)γ-aminopropyltriethoxysilane, γ-aminopropyltrimethoxysilane, γ-aminopropyltriethoxysilane, γ-triethoxy-N-(1,3-dimethyl-butylidene)propylamine, N-phenyl-γ-aminopropyltrimethoxysilane, hydrochloride of N-(vinylbenzil)-β-aminoethyl-γ-aminopropyltrimethoxysilane, and special aminosilane; an ureide silane coupling agent such as γ-ureidopropyltriethoxysilane; a chloropropylsilane coupling agent such as γ-chloropropyltrimethoxysilane; an mercapto silane coupling agent such as γ-mercaptopropyltrimethoxysilane, and γ-mercaptopropylmethyldimethoxysilane; a sulfide silane coupling agent such as bis(triethoxypropyl)tetrasulfide; and an isocyanate silane coupling agent such as γ-isocyanatepropyltriethoxysilane. Among these, γ-methacryloxypropyltriethoxysilane is particularly suitable.

A method for introducing the alkoxysilyl group and/or the isocyanate group to the surface of the substrate by use of the silane coupling agent is not specifically limited. For example, the substrate may be immersed in a solution obtained by dissolving the silane coupling agent in a solvent. The immersion may be preferably carried out in a nitrogen atmosphere.

Further, a temperature of the solution (reaction temperature) is not specifically limited. However, the temperature is preferably in a range of 30° C. or more to 100° C. or less, and more preferably in a range of 40° C. or more to 60° C. or less. Further, the solvent is not specifically limited. For example, a nonpolar organic solvent such as a hydrocarbon solvent such as toluene and hexane is preferably used.

An amount of the silane coupling agent to be used is not specifically limited. However, the amount is preferably in a range of 10% by weight or more to 500% by weight or less, more preferably in a range of 50% by weight or more to 400% by weight or less, and most preferably in a range of 100% by weight or more to 300% by weigh or less.

In a case where the silane coupling agent is used, it is preferable to protect the alkoxysilyl group of the silane coupling agent by use of a surfactant. A method for protecting the silane coupling agent by use of the surfactant is not specifically limited. The surfactant may be mixed with the silane coupling agent. An amount of the surfactant may be in a range of 1.0% by weight or more to 50% by weight or less, and more preferably in a range of 10% by weight or more to 25% by weight or less.

A method for bonding calcium phosphate to the substrate onto which the silane coupling agent is polymerized is not specifically limited. For example, the substrate may be immersed into a solution in which calcium phosphate is suspended. Further, during the immersion, the solution may be stirred. Alternatively, after the immersion, the substrate may be left still under a reduced pressure or preferably in vacuum. Further, the substrate may be heated under the reduced pressure or in vacuum. In this case, a heating temperature is preferably in a range of 50° C. or more to 200° C. or less and more preferably in a range of 80° C. or more to 150° C. or less.

[Cleaning Step]

In the production method of the present invention, the cleaning step may be performed for cleaning a calcium phosphate complex obtained in the bonding step. The cleaning step may be performed depending on a usage/application of the calcium phosphate complex.

A specific cleaning method may be selected as appropriate in accordance with an intended cleaning level. For example, ultrasonic cleaning may be performed. Because the calcium phosphate complex obtained by the production method of the present invention has a remarkably high bonding strength between the substrate and calcium phosphate, peel-off of the calcium phosphate can be favorably prevented even if ultrasonic cleaning is performed. The ultrasonic cleaning may be performed by a conventionally known method.

The production method for producing a calcium phosphate complex as described above may be used for various applications. For example, application of the production method to production of a percutaneous device such as catheter is advantageous. The catheter is not specifically limited. Examples of such a catheter are: a intravenous hyperalimentation catheter; a catheter for treatment of primary pulmonary hypertension; a catheter for a long-term implant extracorporeal circulation system; a permanent external shunt; a catheter for home peritoneal dialysis; and an enteral feeding device. Such a percutaneous device conventionally had a poor adhesion to skin and had a risk of invasion of bacteria into a body through a gap between skin and such a percutaneous device. However, in a case where a member to be fit to the gap between skin and the catheter is made of a calcium phosphate complex, the calcium phosphate complex adheres to the skin. Accordingly, the invasion of bacteria and/or infection can be prevented. Therefore, a catheter significantly excellent in a hygienic aspect can be provided.

The following shows examples and describes the embodiment of the present invention in more detail. The present invention is by no means limited to the examples below and various embodiments that differ in detail are obviously possible. Further, the present invention is not limited to the embodiment described above, but various modifications are possible within the scope of the claims. In addition, an embodiment based on a proper combination of technical means is encompassed in the technical scope of the present invention. Further, all documents cited in the present specifications are hereby incorporated for reference.

EXAMPLES

Example 1

Production of Hydroxyapatite Complex

In the present example, a fiber PET (hereinafter, referred to as "cut PET") was used as a substrate.

Further, the present example employed, as calcium phosphate, a hydroxyapatite sintered body (Hereinafter, this is referred to as a "Hap"; a complex of the substrate and the Hap is referred to as a "hydroxyapatite complex" or "Hap complex"). It should be noted that the Hap was produced according to a method described in Patent Literature 1.

[Ozone Water Treatment]

First, ozone water was produced by using a gas dissolving module (manufactured by Japan Gore-Tex Inc., Model: GT-01T). More specifically, ozone water was produced by bringing tap water (flow rate: 600 mL/min, pressure: 0.05 MPa) and ozone gas (flow rate: 500 mL/min, pressure: 0.03 MPa to 0.05 MPa) in contact with each other within the gas dissolving module.

Next, 600 mg of cut PET was put in a cylinder and ozone water was circulated in the cylinder. That is, while the cut PET was kept immersed in ozone water in the cylinder, ozone water was caused to flow in and out.

In the present example, an ozone concentration of ozone water was set at 17 ppm and a temperature of the ozone water was set at 25° C. A time for which the cut PET was immersed in ozone water was set to 20 minutes. Hereinafter, the time for which the substrate was immersed in ozone water was referred to as an "ozone water treatment time".

Next, after all ozone water flew out, the cut PET was collected by suction filtration.

[Treatment Prior to Graft Polymerization]

The cut PET was put in a doctor test tube. Then, into the doctor test tube, a mixture (a mixture of 500 μL of γ-methacryloxypropyltriethoxysilane (manufactured by Shin-Etsu Chemical Co. Ltd., hereinafter, referred to as "KBE 503") as the silane coupling agent, 73 μL, of pentaethylene glycol dodecyl ether (hereinafter, referred to as "PGDE") as a surfactant, and 18 mL of pure water) was supplied.

Next, the doctor test tube was immersed in liquid nitrogen and liquid inside the doctor test tube was frozen. Then, the doctor test tube was left still for five minutes under a reduced pressure (in vacuuming). Next, while the reduced pressure was maintained, the doctor test tube was immersed in water so that contents inside the doctor test tube melted. Then, nitrogen was sealed in the doctor test tube. The above procedures up to the sealing of nitrogen was repeated one more time, and further, the above procedures up to melting of the mixture was repeated once again (third melting).

[Graft Polymerization]

After the third melting, a graft polymerization reaction was started while the reduced pressure was maintained. More specifically, the doctor test tube was immersed in a temperature-controlled bath and left still at 50° C. for 60 minutes.

[Cleaning Treatment after Graft Polymerization]

The doctor test tube after the graft polymerization was set under an atmospheric pressure and the cut PET was collected by suction filtration. Then, the cut PET was immersed in 200 mL of ethanol and a homopolymer was removed by ultrasonic probe treatment. In the ultrasonic probe treatment, an apparatus manufactured by BRANSON SONIC POWER COMPANY (Model: SONIFIER450) was employed.

Next, while the cut PET is immersed in ethanol, stirring by a stirrer was carried out for 60 minutes. Then, after the cut PET was collected by suction filtration, the cut PET was put in a desiccator and dried under a reduced pressure (in vacuuming, for 60 minutes).

[Adherence of Hap]

Into 20 mL of Hap dispersion solution (concentration: 1 mg/mL, solvent: ethanol), 200 mg of the cut PET was provided. Then, by using an ultrasonic apparatus (manufactured by Kaijo Corporation, Model: CA-24800), ultrasonic treatment at an output of 50 W was performed. Then, the cut PET was collected by suction filtration.

[Annealing of Hap]

The cut PET was left still under a heated and reduced-pressure condition (at 1 kPa (in absolute pressure), at 80° C., for 120 minutes) in a vacuum drier (program-controlled high-temperature vacuum drier, manufactured by Shimizu Scientific Instrument Manufacturing Co. Ltd., Model: VOPC4-3H). Thereby, the Hap was bonded onto the cut PET and the cut PET coated with the Hap was obtained.

[Cleaning after Coating with Hap]

The cut PET coated with the Hap was put in 200 mL of water, and ultrasonic probe treatment was performed for 1 minute. This ultrasonic probe treatment employed the same apparatus as the apparatus used in the ultrasonic probe treatment after the graft polymerization, and was performed by the same method as the ultrasonic probe treatment after the graft polymerization. This ultrasonic probe treatment removed a Hap that had been only adhered to the cut PET but had not been bonded to the cut PET.

Then, while the cut PET was put in water, stirring by a stirrer was performed for 60 minutes. Subsequently, the cut PET was collected by suction filtration and dried in a desiccator under a reduced pressure (in vacuuming, for 60 minutes).

[Observation by Use of Scanning Electron Microscope]

The Hap complex obtained in the present example was observed by use of a scanning electron microscope (manufactured by JEOL Ltd., Model: JSM-5510). FIG. 1 shows results of the observation. FIG. 1 is a diagram illustrating results of observing, by use of the scanning electron microscope, the Hap complex obtained in the present example; (a) of FIG. 1 shows a result of observation at 3,000 times magnification and (b) of FIG. 1 shows a result of observation at 20,000 times magnification.

As shown in FIG. 1, a surface of the cut PET was coated with the Hap uniformly at a high coverage. This shows that a substrate can be coated with a Hap uniformly at a high coverage by treating a surface of the substrate by use of ozone water.

Comparative Example 1

Production of Hydroxyapatite Complex

In the present comparative example, a Hap complex was produced by treating the surface of the substrate by use of an APS initiator (manufactured by Nacalai Tesque Inc.), in stead of treating the surface by use of ozone water.

More specifically, the Hap composite was produced by the same method as in Example 1 except that the following conditions were changed. In other words, in the present comparative example, ozone water treatment was not performed. Further, a mixture of 500 µL of KBE503, 36.5 µL of PGDE, 82 mg of the APS initiator, and 18 mL of water was used as the mixture for polymerization which was prepared in the treatment prior to the graft polymerization.

Comparative Example 2

Production of Hydroxyapatite Composition

A Hap complex was prepared by the same method as in Comparative Example 1 except that a mixture of 1088 µL of KBE503, 292 µL of PGDE, 82 mg of the APS initiator, and 18 mL of water was used as the mixture for polymerization.

Example 2

Comparison of Bonding Strengths

Figure 2:
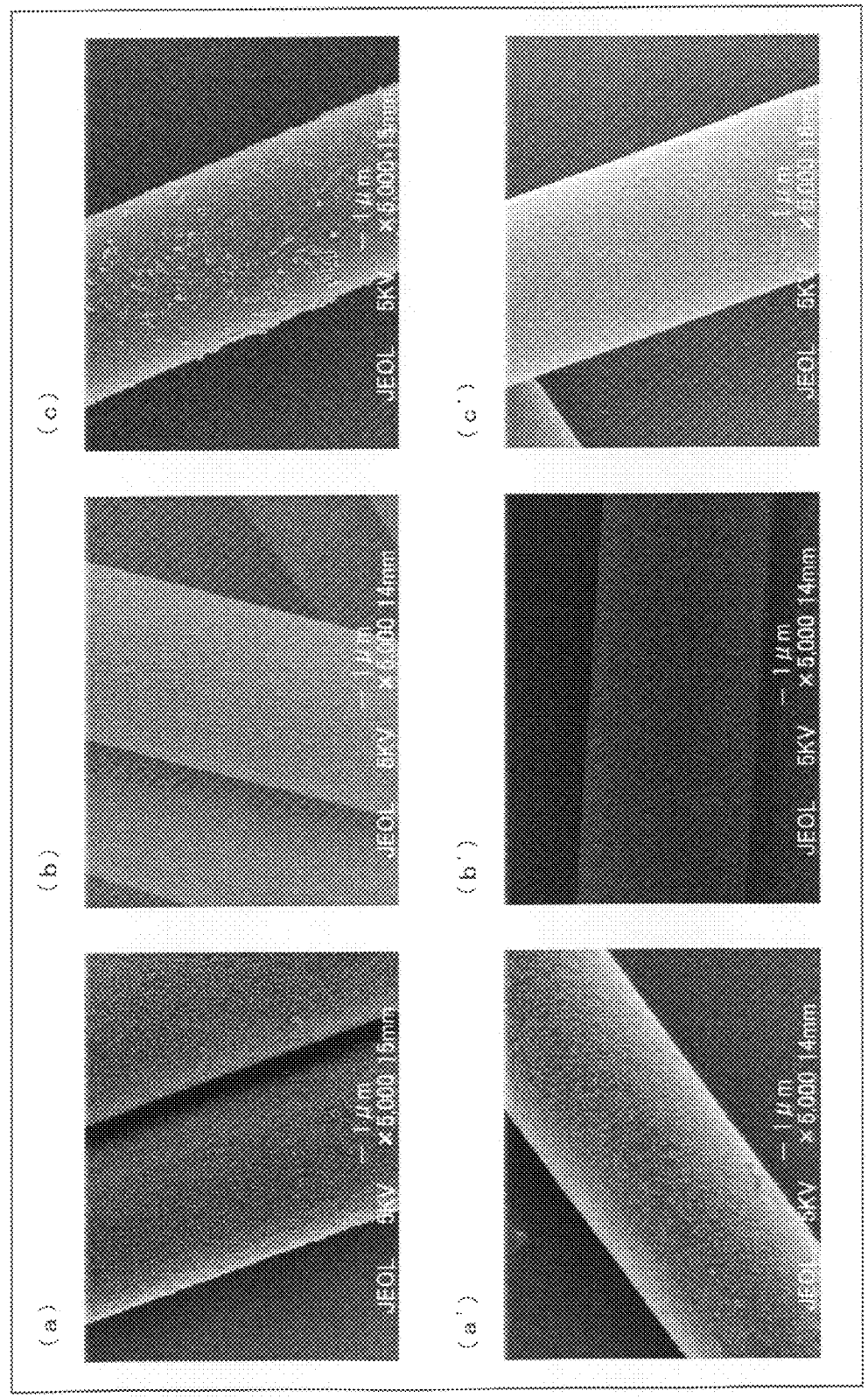
FIG. 2 is a diagram illustrating a result of comparison of bonding strengths of a Hap in Example 2; (a) and (a') of FIG. 2 show a result of observing a surface of cut PET of Example 1; (b) and (b') of FIG. 2 show a result of observing a surface of cut PET of Comparative Example 1; and (c) and (c') of FIG. 2 show a result of observing a surface of cut PET of Comparative Example 2.

Bonding strengths of the Hap were compared, by observing, by use of the scanning microscope, a surface of the cut PET before and after cleaning treatment (ultrasonic probe treatment) following coating with the Hap in each of Example 1 and Comparative Examples 1 and 2. FIG. 2 is a diagram illustrating a result of comparison of the bonding strengths of the Hap in Example 2; (a) and (a') of FIG. 2 show a result of observing the surface of the cut PET of Example 1; (b) and (b') of FIG. 2 show a result of observing the surface of the cut PET of Comparative Example 1; and (c) and (c') of FIG. 2 show a result of observing the surface of the cut PET of Comparative Example 2. Moreover, (a), (b) and (c) of FIG. 2 show results of observing the surfaces of the PET prior to the ultrasonic probe treatment and (a'), (b') and (c') of FIG. 2 show results of observing the surfaces of the PET after the ultrasonic probe treatment.

As shown in FIG. 2, in both cases before and after the ultrasonic probe treatment, the cut PET of Example 1 was coated with Hap uniformly at a higher coverage as compared with the cut PET of each of Comparative Examples 1 and 2. Further, as shown in (a) and (a') of FIG. 2, the cut PET of Example 1 was coated with the Hap uniformly at a high coverage even after the ultrasonic probe treatment. On the other hand, as shown in each of (b), (b'), (c), and (c') of FIG. 2, regarding the cut PET on which the surface treatment by use of APS was performed, much of the Hap was peeled off after the ultrasonic probe treatment. In Comparative Example 1, respective amounts of KBE 503 and PGDE were the same as those in Example 1. However, almost all the Hap was peeled off after the ultrasonic probe treatment. In Comparative Example 2, respective amounts of KBE503 and PGED were larger than those in Example 1. However, much of the Hap was peeled off.

This result indicates that, by treating a surface of a substrate by use of ozone water, it is possible to bond a Hap to a surface of a substrate at a very high bonding strength.

Example 3

Production of Hydroxyapatite Complex

A hydroxyapatite complex was obtained by the same method as in Example 1 except that ozone concentration of ozone water and ozone water treatment time were set in the following four ways. That is, the ozone concentration of ozone water and the ozone water treatment time were set: (a) at 40 ppm for 20 minutes; (b) at 2 ppm for 20 minutes, (c) at 40 ppm for 5 minutes; and (d) at 2 ppm for 5 minutes.

Figure 3:
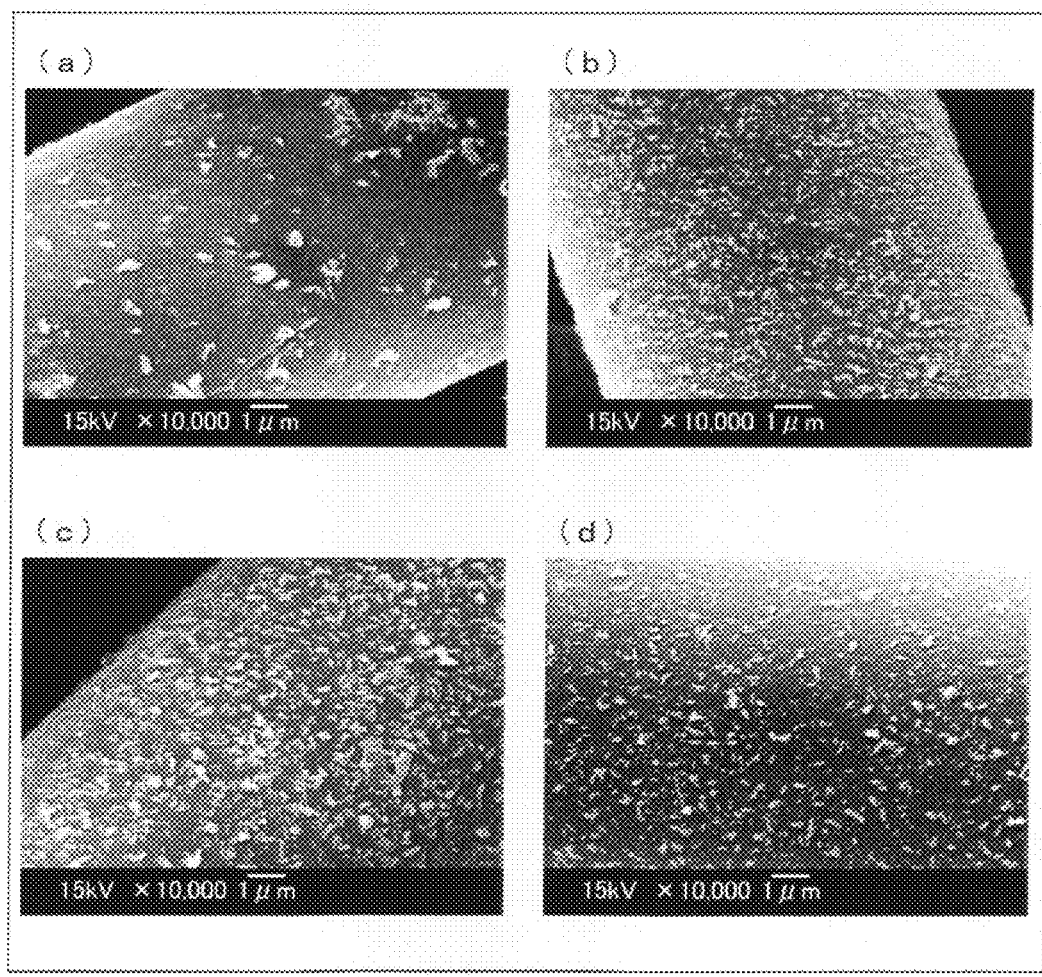
FIG. 3 is a diagram illustrating results of observing, by use of a scanning electron microscope, surfaces of four kinds of hydroxyapatite complexes obtained in Example 3; (a) of FIG. 3 shows a result in a case where an ozone concentration of ozone water was 40 ppm and a time for ozone water treatment was 20 minutes; (b) of FIG. 3 shows a result in a case where the ozone concentration of ozone water was 2 ppm and the time for the ozone water treatment was 20 minutes; (c) of FIG. 3 shows a result in a case where the ozone concentration of ozone water was 40 ppm and the time for the ozone water treatment was 5 minutes; and (d) of FIG. 3 shows a result in a case where the ozone concentration of ozone water was 2 ppm and the time for the ozone water treatment was 5 minutes.

FIG. 3 shows results of observing, by use of the scanning electron microscope, respective surfaces of hydroxyapatite complexes. FIG. 3 is a diagram illustrating results of observing, by use of the scanning electron microscope, the surfaces of four kinds of the hydroxyapatite complexes obtained in the present example; (a) of FIG. 3 shows a result in a case where the ozone concentration of ozone water was 40 ppm and the ozone water treatment time was 20 minutes; (b) of FIG. 3 shows a result in a case where the ozone concentration of ozone water was 2 ppm and the ozone water treatment time was 20 minutes; (c) of FIG. 3 shows a result in a case where the ozone concentration of ozone water was 40 ppm and the ozone water treatment time was 5 minutes; and (d) of FIG. 3 shows a result in a case where the ozone concentration of ozone water was 2 ppm and the ozone water treatment time was 5 minutes.

As shown in FIG. 3, in each condition, the Hap was favorably adhered to the surface of each cut PET. Particularly in cases of (b) and (c) of FIG. 3, the hydroxyapatite complexes obtained each had a very high coverage and a very high bonding strength. This shows that: (i) when the ozone concentration of ozone water is high, a shorter ozone treatment time is preferable; whereas (ii) when the ozone concentration of ozone water is low, a longer ozone treatment time is preferable.

Example 4

Production of Hydroxyapatite Complex

In the present example, as the substrate, a silk fibroin fiber (manufactured by Fujimura Seishi Co. Ltd., and hereinafter, referred to as "cut silk") was used, and a Hap complex was produced by the same method as in Example 1 except that the following conditions were changed.

That is, the ozone concentration of ozone water was set at 27 ppm.

A mixture of 323 μL of KBE503, 36.5 μL of PGDE, and 18 mL of pure water was used as the mixture for polymerization.

In polymerization treatment, conditions at the time when the doctor test tube was immersed in the temperature-controlled bath were set at 40° C. for 30 minutes.

When the Hap was adhered, ultrasonic treatment time was set to 5 minutes.

When annealing of the Hap was carried out, conditions for the heated and reduced-pressure condition were set at 120° C. for 120 minutes.

The cleaning treatment after coating with the Hap employed, in place of water, ethanol solution that was a mixture of ethanol and water. In the ethanol solution, a volume proportion of ethanol to water was 3:1.

Example 5

Production of Hydroxyapatite Complex

A Hap complex was produced by the same method as in Example 4 except that the ozone concentration of ozone water was set at 35 ppm.

Example 6

Comparison of Influence of Ozone Concentration of Ozone Water on Silk Surface

Figure 4:
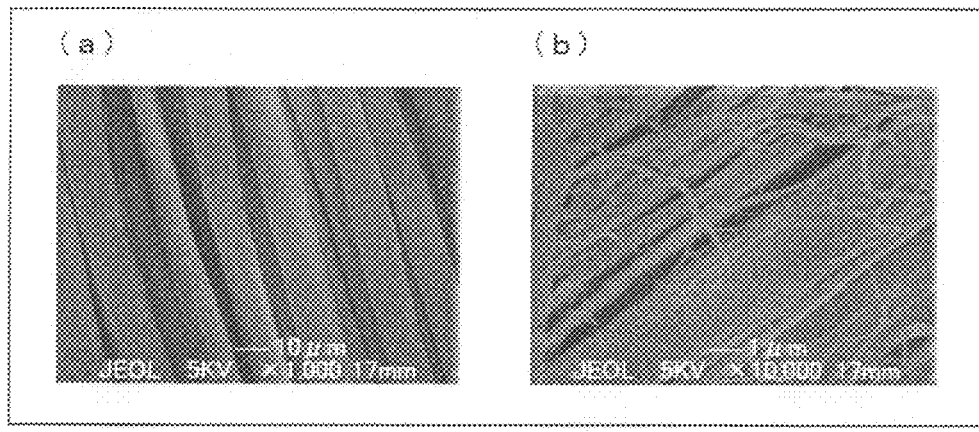
FIG. 4 is a diagram illustrating results of observing, by use of a scanning electron microscope, cut silk right after ozone water treatment in each of Examples 4 and 5; (a) of FIG. 4 shows a result of observation of the cut silk in Example 4 and (b) of FIG. 4 shows a result of observation of the cut silk in Example 5.

In the present example, how ozone water used in the ozone water treatment influenced cut silk was examined. More specifically, cut silk surfaces right after the ozone water treatment was observed by use of the scanning electron microscope. FIG. 4 shows results of the observation. FIG. 4 is a diagram illustrating results of observing, by use of the scanning electron microscope, cut silk right after ozone water treatment in each of Examples 4 and 5; (a) of FIG. 4 shows a result of observation of the cut silk in Example 4 and (b) of FIG. 4 shows a result of observation of the cut silk in Example 5.

As shown in FIG. 4, the cut silk surface was not damaged when the ozone concentration of ozone water was 27 ppm.

Example 7

Evaluation of Hydroxyapatite Complex

Figure 5:
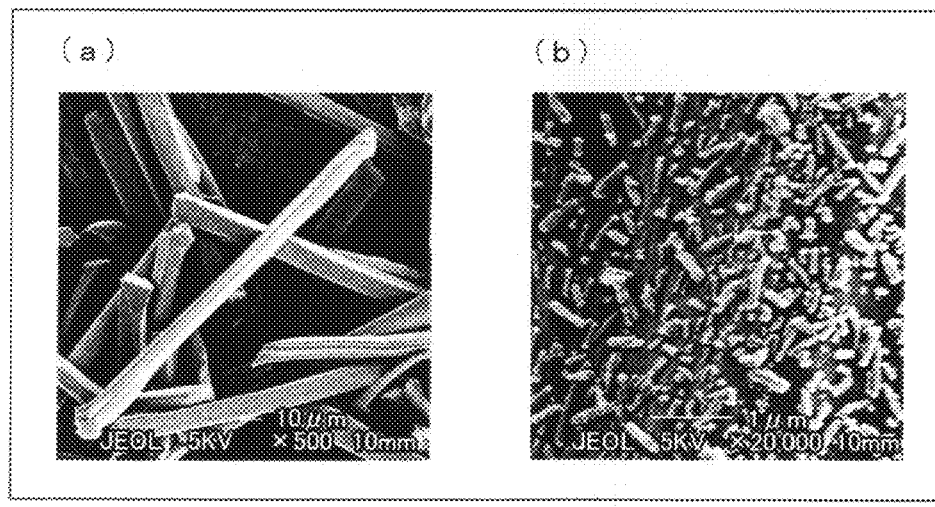
FIG. 5 is a diagram illustrating results of observing, by use of a scanning electron microscope, states before and after bonding a Hap to cut silk in Example 4; (a) of FIG. 5 shows a result of observation of the cut silk right after graft polymerization and (b) of FIG. 5 shows a result of observation of a Hap complex obtained by bonding the Hap to the cut silk.
Figure 6:
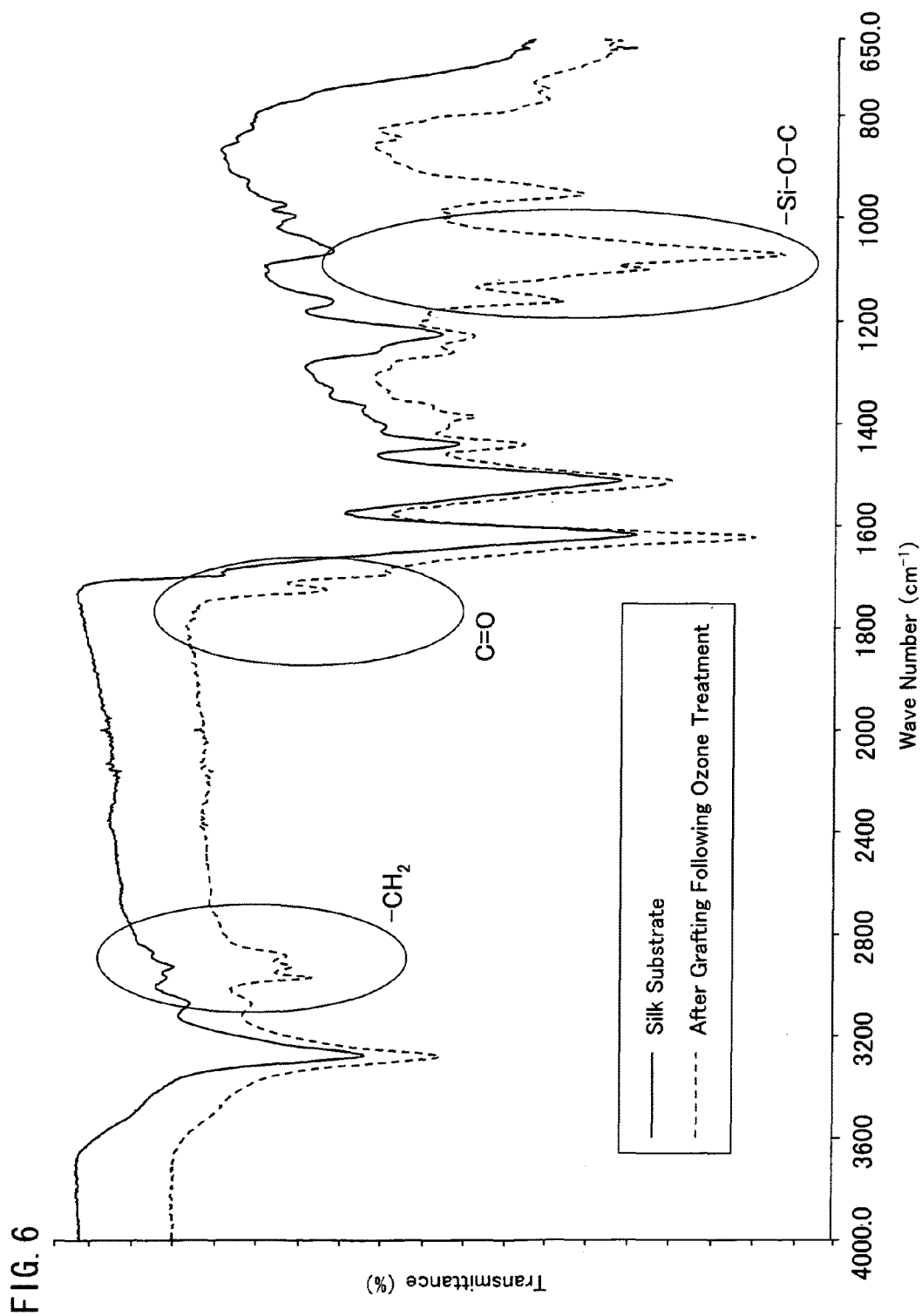
FIG. 6 is a diagram illustrating a result of analyzing, by FT-IR, the cut silk of Example 4.

The Hap complex obtained in Example 4 was evaluated. More specifically, the Hap complex was observed by using the scanning electron microscope and analyzed by FT-IR. FIGS. 5 and 6 show results of the evaluation. FIG. 5 is a diagram illustrating results of observing, by use of the scanning electron microscope, states before and after bonding a Hap to the cut silk in Example 4; (a) of FIG. 5 shows a result of observation of the cut silk right after graft polymerization and (b) of FIG. 5 shows a result of observation of the Hap complex obtained. FIG. 6 shows a result of analyzing, by FT-IR, the cut silk of Example 4. In FIG. 6, a horizontal axis indicates wavelength (cm-1) and a vertical axis indicates transmittance (%). Further, a spectrum indicated by a line in FIG. 6 shows a spectrum before the graft polymerization and a spectrum indicated by a dotted line indicates a spectrum of the cut silk after the graft polymerization.

As shown in FIG. 5, by treating a surface of the cut silk by use of ozone water, the cut silk could be coated with the Hap uniformly at a high coverage. Further, as shown in FIG. 6, by treating the surface of the cut silk by use of ozone water, the cut silk and KBE 503 were favorably graft-polymerized.

Example 8

Comparison of Amounts of Respective Residues

In the present example, an amount of each residue after the graft polymerization and an amount of each residue after cleaning following the graft polymerization were compared.

Hydroxyapatite complexes used for the comparison were obtained as follows. A hydroxyapatite complex of the present example was produced by the same method as in Example 4 except that a composition of reaction solution for polymerization was arranged as shown in Table 1 as explained later (Hereinafter, the hydroxyapatite complex thus obtained is referred to as "Example 8'".

The hydroxyapatite complexes to be compared were calcium phosphate complexes respectively obtained by the same method as Example 8' except that two kinds of compositions of reaction solution for polymerization were arranged as shown in Table 1 explained later. Two kinds of these hydroxyapatite complexes are referred to as "Comparative Example 3" and "Comparative Example 4", respectively.

Further, in the present example, based on the amount of each residue in waste solution left after the graft polymerization and the amount of each residue in waste solution left after the cleaning, an amount of a silane coupling agent and the like used in the graft polymerization was calculated. Note that the amount of each residue was calculated by measuring a weight of a substance that remained after water and ethanol had been evaporated by use of a vacuum drier from the waste solution that had been filtered. Table 1 shows a result of the calculation.

TABLE 1

| | | Example 8' | Comparative Example 3 | Comparative Example 4 |
|---|---|---|---|---|
| Composition of Reaction Solution for Polymerization | KBE503 | 0.329 g | 0.329 g | 1.113 g |
| | APS | — | 0.082 g | 0.082 g |
| | PGDE | 0.0916 g | 0.0916 g | 0.3145 g |
| Amount (a) of Residue Right After Graft Polymerization | | 0.1681 g | 0.2886 g | 0.7869 g |
| Amount (b) of Residue After Cleaning Following Graft Polymerization | | 0.0021 g | 0.0148 g | 0.0124 g |
| Total Amount (a + b) of Residues | | 0.1702 g | 0.3034 g | 0.7993 g |
| Value (c) Obtained by Subtracting, From Total Amount of Residue, Weight of PGDE and APS in Residue | | 0.0786 g | 0.1298 g | 0.4028 g |
| Weight of KBE503 Used In Graft Polymerization (Value Obtained By Subtracting c from Weight of KBE503 Used) | | 0.2504 g | 0.1301 g | 0.7102 g |

It should be noted that Comparative Example 4 employed a conventional method, whereas Comparative Example 3 employed a method according to which respective amounts of KBE503 and PGDE were arranged to be the same as those of Example 8' in the composition of the reaction solution of Comparative Example 4.

In Comparative Example 3, whereas the amount of KBE503 is 29.6% with respect to the amount of KBE503 in Comparative Example 4, the amount of the residue (value c) is 32.2% with respect to the amount of the residue in Comparative Example 4. This point can be considered to be within a range of error. The above point may also be considered to have occurred for the following reason. That is, because an amount of APS was excessive with respect to monomers in Comparative Example 4, polymerization of monomers progressed in the solution regardless of silk fibroin and consequently a slightly larger amount of homopolymers were produced.

As shown in Table 1, the total amount of residues of Example 8' was less than those of Comparative Examples 3 and 4. Further, though the same amount of KBE503 was used in Example 8' and Comparative Example 3, a larger amount of KBE503 was used in the graft polymerization in Example 8' as compared with Comparative Example 3. This result shows that, by treating a surface by use of ozone water, it is possible to reduce an amount of residue produced, in particular, an amount of a residual silane coupling agent. It should be noted that, because KBE503 has a hydrophilic group, it is difficult to completely remove water from the residues. Therefore, the respective amounts of the residues shown in Table 1 each include a weight of water. Even in consideration of inclusion of water in the residues, most of the residues are a surfactant. The surfactant becomes insoluble in most solvent such as water when the surfactant reacts with the silane coupling agent. Further, the surfactant can easily be separated from a mixture of the surfactant and the silane coupling agent. Therefore, according to the present invention, the surfactant can be recycled. However, according to the conventional method, an inorganic salt is mixed in because APS is used. In many cases, the inorganic salt is a sulfonate. When the inorganic salt mixes in, the surfactant becomes soluble in water and/or water-soluble solvent. As a result, the separation of the surfactant becomes difficult.

It should be noted that "Weight of KBE503 Used In Graft Polymerization" shown in Table 1 is merely a measure and means a theoretical maximum amount of monomers used in the graft polymerization. For example, a substance that can be collected as a residue is a monomer or an oligomer of an amount that can be dissolved or suspended in a medium. Therefore, it is not easy to remove, from the calcium phosphate complex, a homopolymer that is insolubilized by polymerization. Therefore, the present invention in which the silane coupling agent is efficiently used in the graft polymerization is advantageous in a point such that an amount of such a homopolymer produced is small.

Comparative Example 3

Surface Treatment by Use of Ozone Gas

Figure 7:
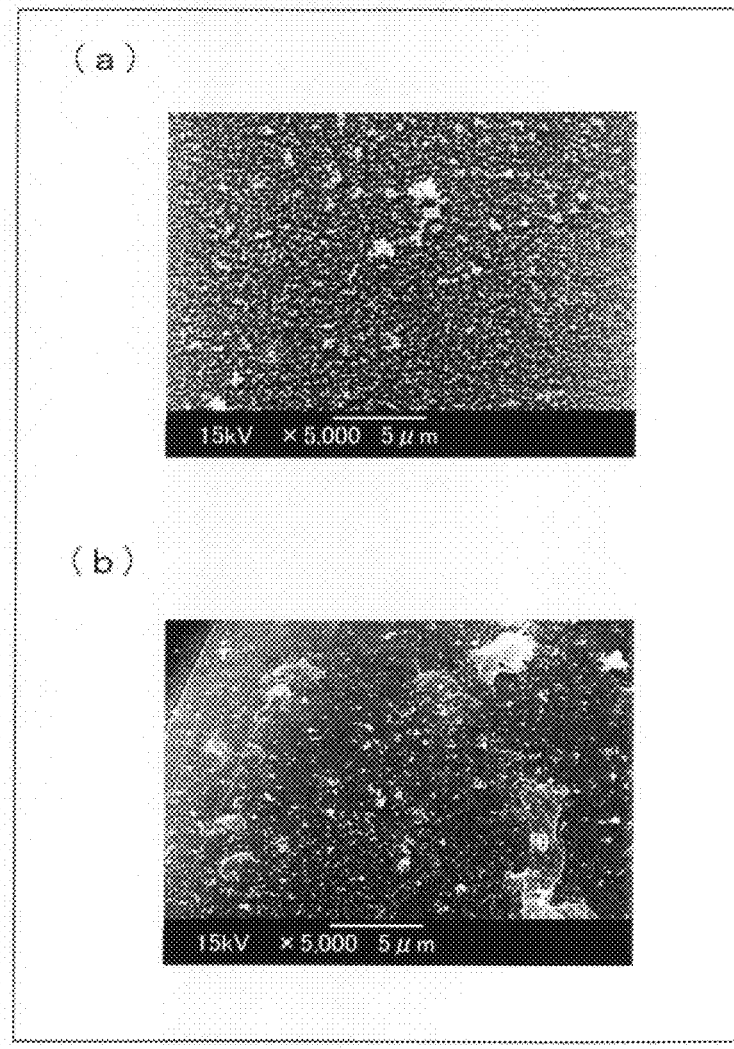
FIG. 7 is a diagram illustrating results of observing a surface of PET coated with the Hap by use of ozone gas instead of treating the surface by use of ozone water in Comparative Example 3; (a) of FIG. 7 shows a result of observation of the surface of a substrate before ultrasonic probe treatment and (b) of FIG. 7 shows a result of observation of the surface of the substrate after the ultrasonic probe treatment.

A surface of the substrate (pet) was treated by use of ozone gas, instead of treating the surface by use of ozone water. More specifically, instead of treating the surface by use of ozone water, ozone gas was brought into contact with PET. Except this, the same procedures as in Example 1 were performed. FIG. 7 shows results. FIG. 7 is a diagram illustrating results of observing a surface of PET coated with the Hap by treating the surface by use of ozone gas (ozone gas: 70% by weight, for 20 minutes) instead of treating the surface by use of ozone water; (a) of FIG. 7 shows a result of observation of the surface of a substrate before ultrasonic probe treatment and (b) of FIG. 7 shows a result of observation of the surface of the substrate after the ultrasonic probe treatment.

As shown in FIG. 7, from the surface of the substrate after the ultrasonic probe treatment, a large amount of Hap particles were peeled off. In other words, in the case where the surface of the substrate was treated by use of ozone gas, a Hap complex could not be produced because a radical could not be efficiently introduced. Conceivable reasons for this situation are as follows: (i) because an efficiency of a contact between ozone gas and the substrate was much poorer than that in the case where ozone water was employed, the Hap particles were only physically adhered to the substrate; and (ii) ozone gas could not sufficiently supply oxygen radicals.

From this result, it was proved that, in the production of the Hap complex, the treatment of the surface of the substrate by use of ozone water is much superior means to the treatment of the surface by use of ozone gas.

Example 9

Comparison in Regard to Ozone Concentration of Ozone Water

In the present example, a hydroxyapatite complex was produced by the same method as in Example 1 except that an ozone concentration of ozone water was arranged to be higher than those in Examples 1 and 3. In other words, the ozone concentration of ozone water was set at 80 ppm. FIG. 8 shows a result.

FIG. 8 is a diagram illustrating results of observation of the Hap complex before and after ultrasonic probe treatment in the present example; (a) and (b) of FIG. 8 show a result of observation of the Hap complex before the ultrasonic probe treatment and (a') and (b') of FIG. 8 show a result of observation of the Hap complex after the ultrasonic probe treatment. Note that (a) and (a') of FIG. 8 show the results of observation at 5,000 times magnification and (b) and (b') of FIG. 8 show the results of observation at 1,000 times magnification.

Figure 9:
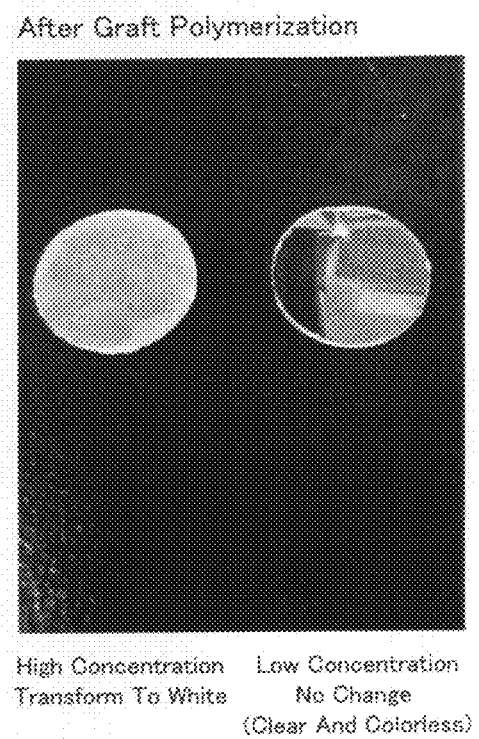
FIG. 9 shows a result of observation of surfaces of substrates (in the cases of high concentration and low concentration) after graft polymerization in Example 9.

Further, FIG. 9 shows a result of observing surfaces of substrates after graft polymerization. FIG. 9 shows the result of the observation of the surfaces; a left circle shows a result of observing a surface of a substrate in the case where the ozone concentration of ozone water was set at a high concentration (80 ppm) and a right circle shows a result of observing a surface of a substrate in the case where the ozone concentration of ozone water was set at a low concentration (0.8 ppm).

The results shown in (a') and (b') of FIG. 8 show that the surface of the substrate was coated with the Hap even when the ozone concentration of ozone water was set at a high concentration in the present example. However, in a comparison between the surface of the substrate shown in (a') and (b') of FIG. 8 and the surface of the substrate shown in FIG. 9 after the graft polymerization (in a case where the concentration of the ozone water was set high), the surface of the substrate after the ultrasonic probe treatment was more clouded in the case where the ozone concentration of ozone water was set high. It was also observed that a crack occurred on the surface of the substrate.

Example 10

Comparison in Regard to Ozone Concentration of Ozone Water

In the present example, a hydroxyapatite complex was produced by the same method as in Example 1 except that an ozone concentration of ozone water was arranged to be lower than those in Examples 1 and 3. In other words, the ozone concentration of ozone water was set at 0.8 ppm. FIG. 9 shows a result.

Figure 10:
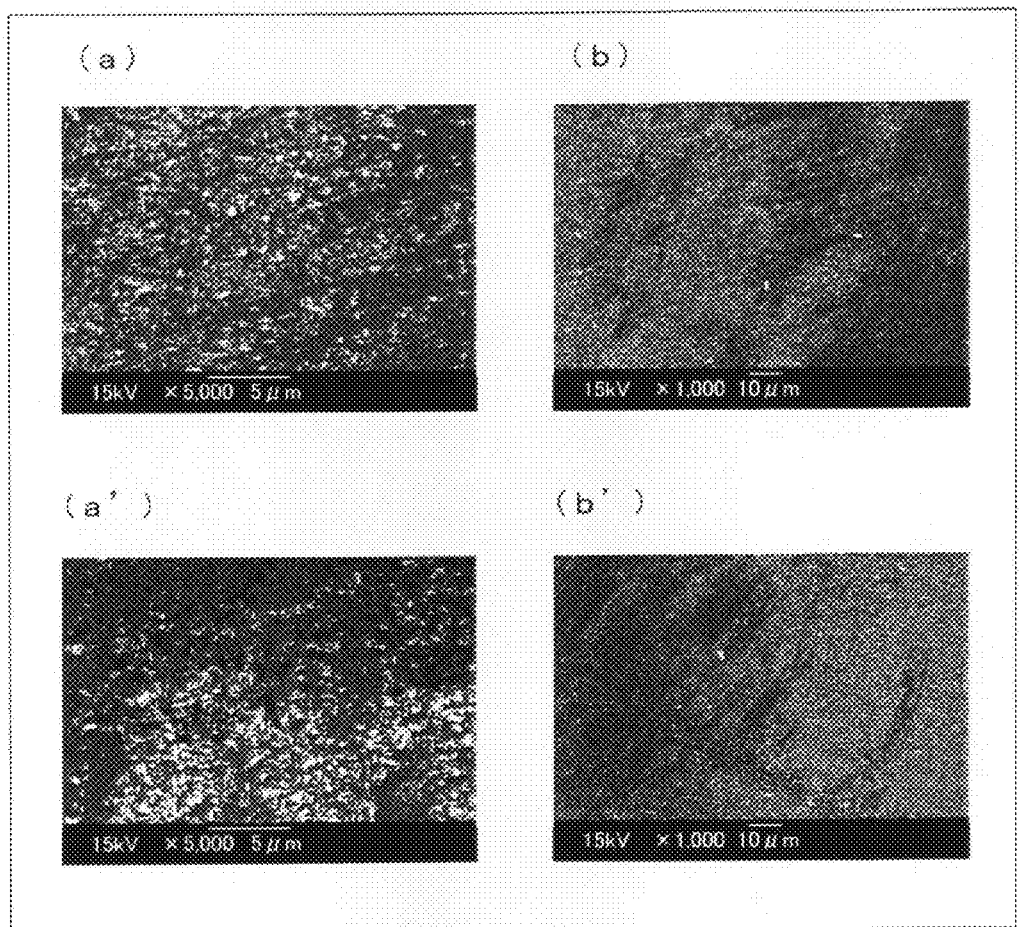
FIG. 10 is a diagram illustrating results of observation of a surface of a hydroxyapatite complex obtained in Example 10; (a) and (b) of FIG. 10 show a result of observation of the surface of the hydroxyapatite complex before the ultrasonic probe treatment and (a') and (b') of FIG. 10 show a result of observation of the surface of the hydroxyapatite complex after the ultrasonic probe treatment.

FIG. 10 is a diagram illustrating results of observation of a surface of the hydroxyapatite complex obtained in Example 10; (a) and (b) of FIG. 10 show a result of observation of the surface of the hydroxyapatite complex before the ultrasonic probe treatment and (a') and (b') of FIG. 10 show a result of observation of the surface of the hydroxyapatite complex after the ultrasonic probe treatment. Note that (a) and (a') of FIG. 10 show the results of observation at 5,000 times magnification and (b) and (b') of FIG. 10 show the results of observation at 1,000 times magnification.

The results shown in (a') and (b') of FIG. 10 show that the surface of the substrate was coated with the Hap even when the ozone concentration of ozone water was set at a low concentration in the present example. However, in the observation, the coating of Hap particles was uneven on the surface of the substrate coated with the Hap in the present example.

In this way, from each of the hydroxyapatite complexes of Examples 9 and 10, it was found that the surface of the substrate is coated with the Hap particles even in a case where the ozone concentration of ozone water is set at 0.8 ppm or 80 ppm. However, it was also found that, in such a case, a crack may occur on the surface of the substrate and the coating of the Hap particles may become uneven.

Example 11

Production of Hydroxyapatite Complex

In the present example, a hydroxyapatite complex was produced by the same method as in Example 1 except that polyurethane was used as a substrate and various conditions were changed. More specifically, in Example 11, five plate substrates each having a diameter of 15 mm were used. Regarding a condition for ozone water treatment, an ozone concentration of ozone water was set at 15 ppm. Further, regarding a condition for graft polymerization, PGDE was set to 36.5 μL. In addition, in adherence of the Hap, two substrates (plates each having a diameter of 15 mm) after the graft polymerization were treated by 20 mL of dispersion solution.

Figure 11:
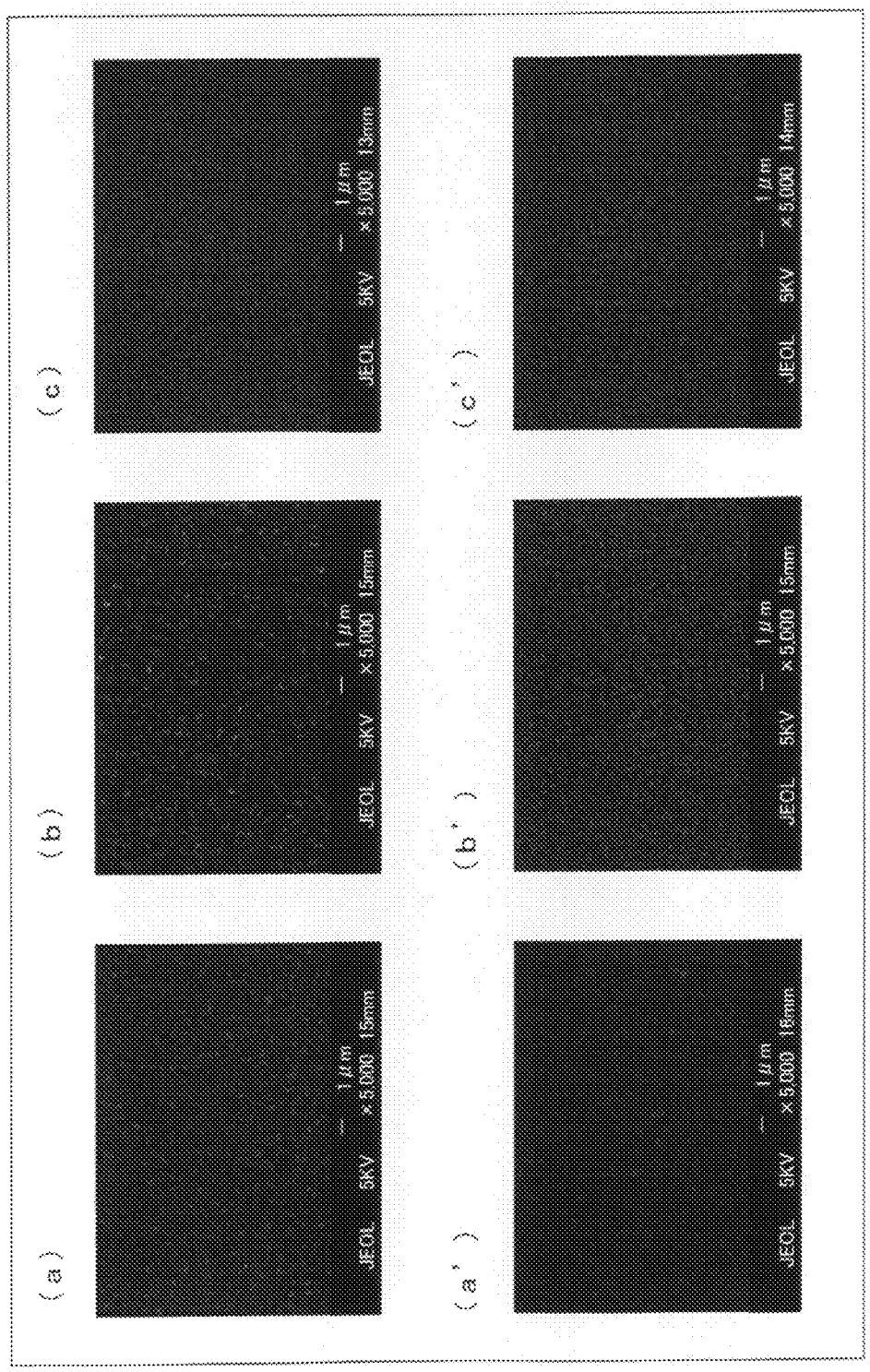
FIG. 11 is a diagram illustrating results of observation of surfaces of hydroxyapatite complexes obtained in Example 11 before and after ultrasonic probe treatment; (a), (b), and (c) of FIG. 11 show a result of observation of the surfaces of the hydroxyapatite complexes before the ultrasonic probe treatment and (a'), (b'), and (c') of FIG. 11 show a result of observation of the surfaces of the hydroxyapatite complexes after the ultrasonic probe treatment.

Comparative Hap complexes used for comparison were: (i) a Hap complex (referred to as "Comparative Example 5") obtained by using polyurethane as a substrate and directly coating, with the Hap, the substrate that had been subjected to none of ozone water treatment and graft polymerization and (ii) a Hap complex (referred to as "Comparative Example 6") obtained by using polyurethane as a substrate and coating, with the Hap, a surface of the substrate whose surface had been treated by use of an APS initiator (radical initiator) and graft-polymerized. FIG. 11 shows a result.

FIG. 11 is a diagram illustrating results of observation of surfaces of hydroxyapatite complexes obtained in the present example before and after ultrasonic probe treatment; (a), (b), and (c) of FIG. 11 show a result of observation of the surfaces of the hydroxyapatite complexes before the ultrasonic probe treatment and (a'), (b'), and (c') of FIG. 11 show a result of observation of the surfaces of the hydroxyapatite complexes after the ultrasonic probe treatment. It should be noted that (a) and (a') of FIG. 11 shows the results in the case of Comparative Example 5; (b) and (b') of FIG. 11 shows the results in the case of Example 11; and (c) and (c') of FIG. 11 shows the results in the case of Comparative Example 6.

As shown in FIG. 11, when the Hap coated the substrate that had been subjected to none of ozone water treatment and graft polymerization, a bonding strength of the Hap to the surface of the substrate was weak as compared with a case where the ozone water treatment and the graft polymerization were performed. Further, in a case where the ozone water treatment was performed, the coating of the Hap was more favorable as compared with a case where the APS initiator was used.

Example 12

Production of Hydroxyapatite Complex

In the present example, a hydroxyapatite complex was produced by the same method as in Example 11 except that polymethylmethacrylate was used as a substrate.

Figure 12:
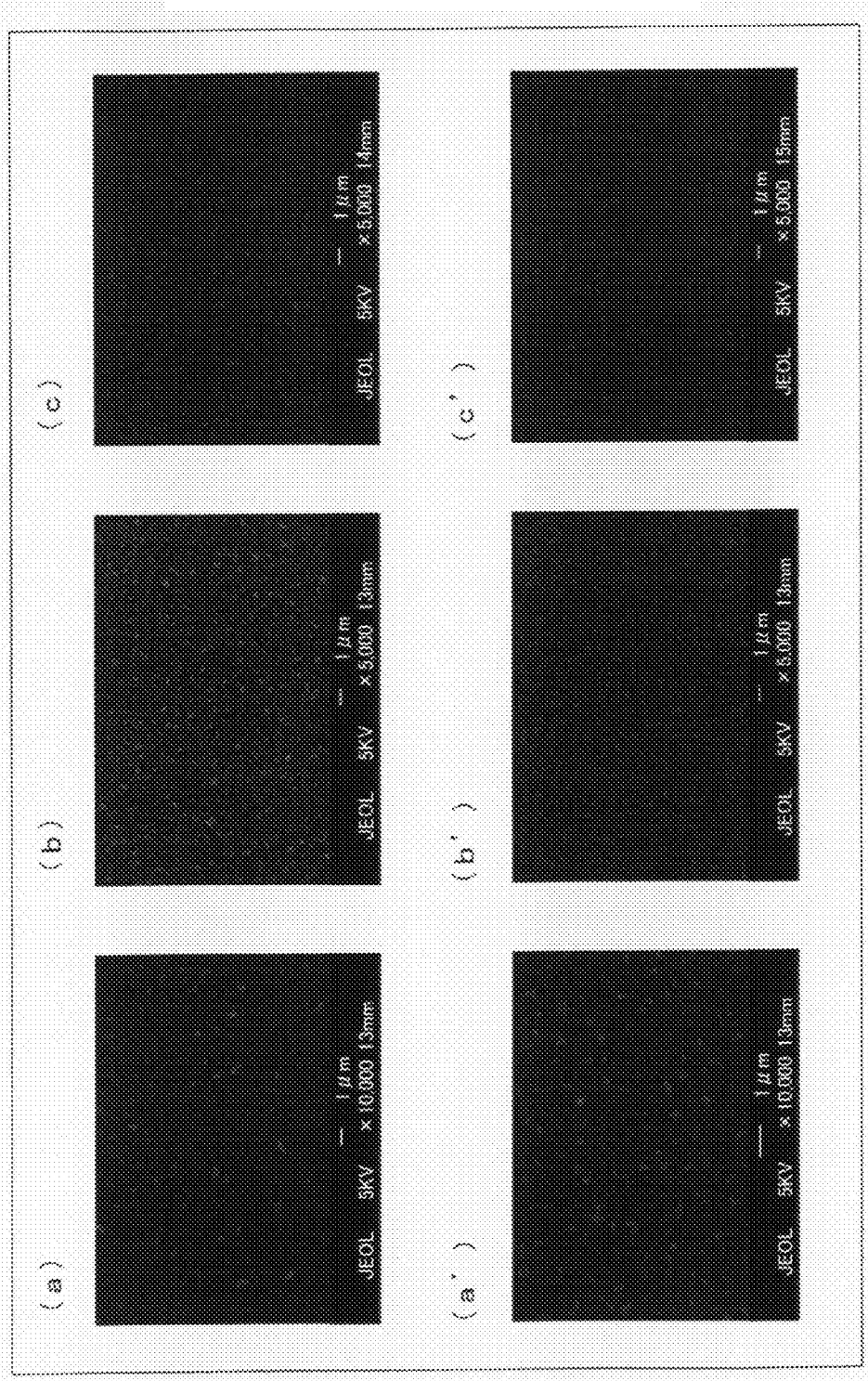
FIG. 12 is a diagram illustrating results of observation of a surface of a hydroxyapatite complex obtained in Example 12 and comparative surfaces before and after ultrasonic probe treatment; (a), (b), and (c) of FIG. 12 show a result of observation of the surface of the hydroxyapatite complex and the comparative surfaces before the ultrasonic probe treatment and (a'), (b') and (c') of FIG. 12 show a result of observation of the surface of the hydroxyapatite complex and the comparative surfaces after the ultrasonic probe treatment.

Comparative Hap complexes used for comparison were: (i) a Hap complex (referred to as "Comparative Example 7") obtained by using polymethylmethacrylate as a substrate and directly coating, with the Hap, the substrate that had been subjected to none of ozone water treatment and graft polymerization and (ii) a Hap complex (referred to as "Comparative Example 8") obtained by using polymethylmethacrylate as a substrate and coating, with the Hap, a surface of the substrate whose surface had been treated by use of an APS initiator (radical initiator) and graft-polymerized. FIG. 12 shows a result.

FIG. 12 is a diagram illustrating results of observation of the surface of the hydroxyapatite complex obtained in the present example and comparative surfaces before and after ultrasonic probe treatment; (a), (b), and (c) of FIG. 12 show a result of observation of the surface of the hydroxyapatite complex and the comparative surfaces before the ultrasonic probe treatment and (a'), (b') and (c') of FIG. 12 show a result of observation of the surface of the hydroxyapatite complex and the comparative surfaces after the ultrasonic probe treatment. It should be noted that (a) and (a') of FIG. 12 show the results in the case of Comparative Example 7, and (b) and (b') of FIG. 12 show the result in the case of Example 12 and (c) and (c') of FIG. 12 show the result in the case of Comparative Example 8.

As shown in FIG. 12, when the Hap coated the substrate that had been subjected to none of ozone water treatment and graft polymerization, a bonding strength of the Hap to the surface of the substrate was weak as compared with a case where the ozone water treatment and the graft polymerization were performed. It should be noted that, in a case where the ozone water treatment was performed, the coating of the Hap was similar to that in a case where the APS initiator was used.

Example 13

Production of Hydroxyapatite Complex

In the present example, a hydroxyapatite complex was produced by the same method as in Example 1 except that silicone was used as a substrate and various conditions were changed. That is, in the present example, an ozone concentration of ozone water was set at 15 ppm. Further, 18 mL of 10% by weight acrylic acid was used as an agent for graft polymerization in place of the silane coupling agent (KBE) and a polymerization reaction was carried out for 10 minutes. Acrylic acid was used as the graft polymerization agent in the present example. This is because silicone includes a lot of oxygen atoms and therefore the polymerization reaction will be inhibited in a case where KBE is used.

Figure 13:
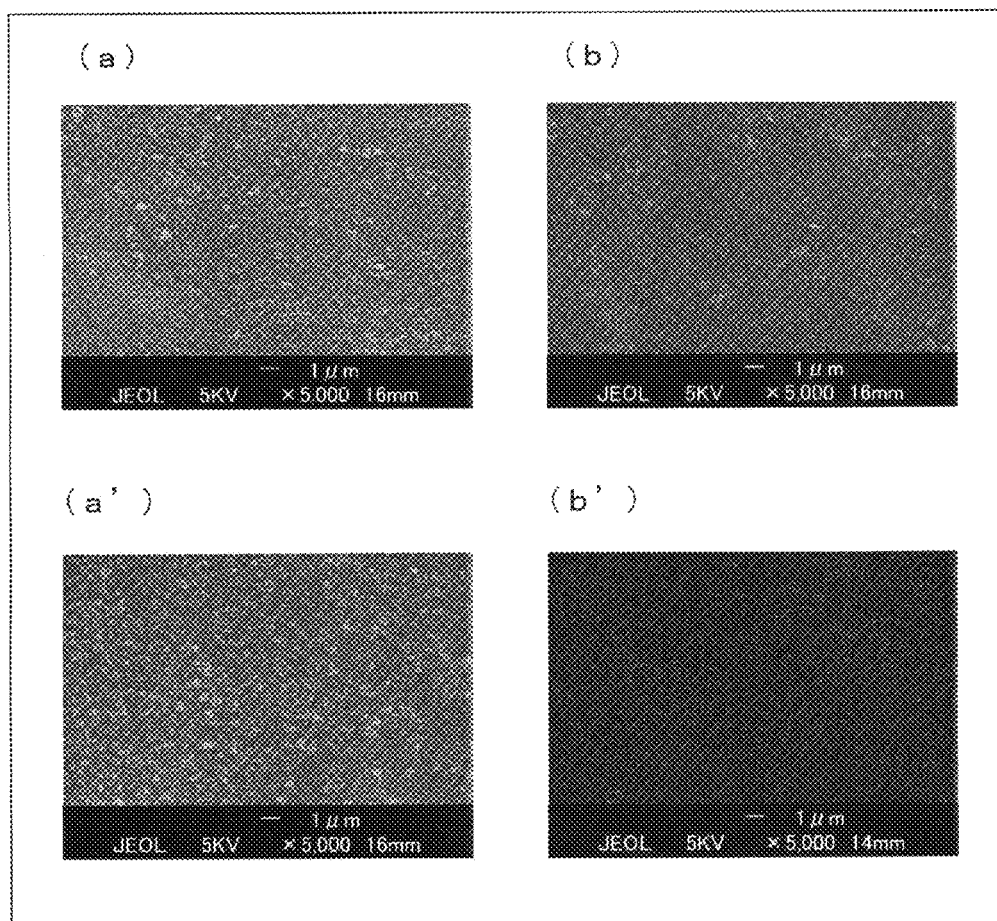
FIG. 13 is a diagram illustrating results of observation of a surface of a Hap complex obtained in Example 13 and a surface of Comparative Example 9 before and after ultrasonic probe treatment; (a) and (b) of FIG. 13 show a result of observation of the surfaces of the hydroxyapatite complexes before the ultrasonic probe treatment and (a') and (b') of FIG. 13 show a result of observation of the surfaces of the hydroxyapatite complexes after the ultrasonic probe treatment.

A comparative Hap complex used in the comparison was a hydroxyapatite complex obtained by the same method as in Example 1 except that the Hap directly coated the substrate that had not been subjected to the graft polymerization. This Hap complex is referred to as "Comparative Example 9". FIG. 13 shows a result of the comparison.

FIG. 13 is a diagram illustrating results of observation of a surface of the Hap complex obtained in the present example and a surface of Comparative Example 9 before and after ultrasonic probe treatment; (a) and (b) of FIG. 13 show a result of observation of the surfaces of the hydroxyapatite complexes before the ultrasonic probe treatment and (a') and (b') of FIG. 13 show a result of observation of the surfaces of the hydroxyapatite complexes after the ultrasonic probe treatment. It should be noted that (a) and (a') of FIG. 13 show the Hap complex obtained in the present example and (b) and (b') of FIG. 13 show Comparative Example 9.

As shown in FIG. 13, before the ultrasonic probe treatment, the Hap coating was preferable in the Hap complex of Example 13. However, in the case of Comparative Example 9, an amount of the Hap coating was smaller. Further, after the ultrasonic probe treatment, in the case of Comparative Example 9, it was observed that the Hap particles had been peeled off. However, in the case of the Hap complex of Example 13, it was not observed that the Hap particles had been peeled off.

This showed that, in a case where silicone is used as a substrate, Hap coating becomes preferable when the substrate has been treated by use of acrylic acid rather than directly coated with the Hap. This also showed that because the Hap adheres to the substrate not physically but chemically as a result of the treatment with use of acrylic acid, the Hap particles can be prevented from being peeled off even in a case where the ultrasonic probe treatment is performed on the substrate.

Example 14

Production of Hydroxyapatite Complex

In the present example, a hydroxyapatite complex was produced by the same method as in Example 1 except that polystyrene was used as a substrate and a bonding strength of the hydroxyapatite complex thus obtained was compared. It should be noted that because polystyrene makes KBE soluble, acrylic acid was used as an agent for graft polymerization.

Figure 14:
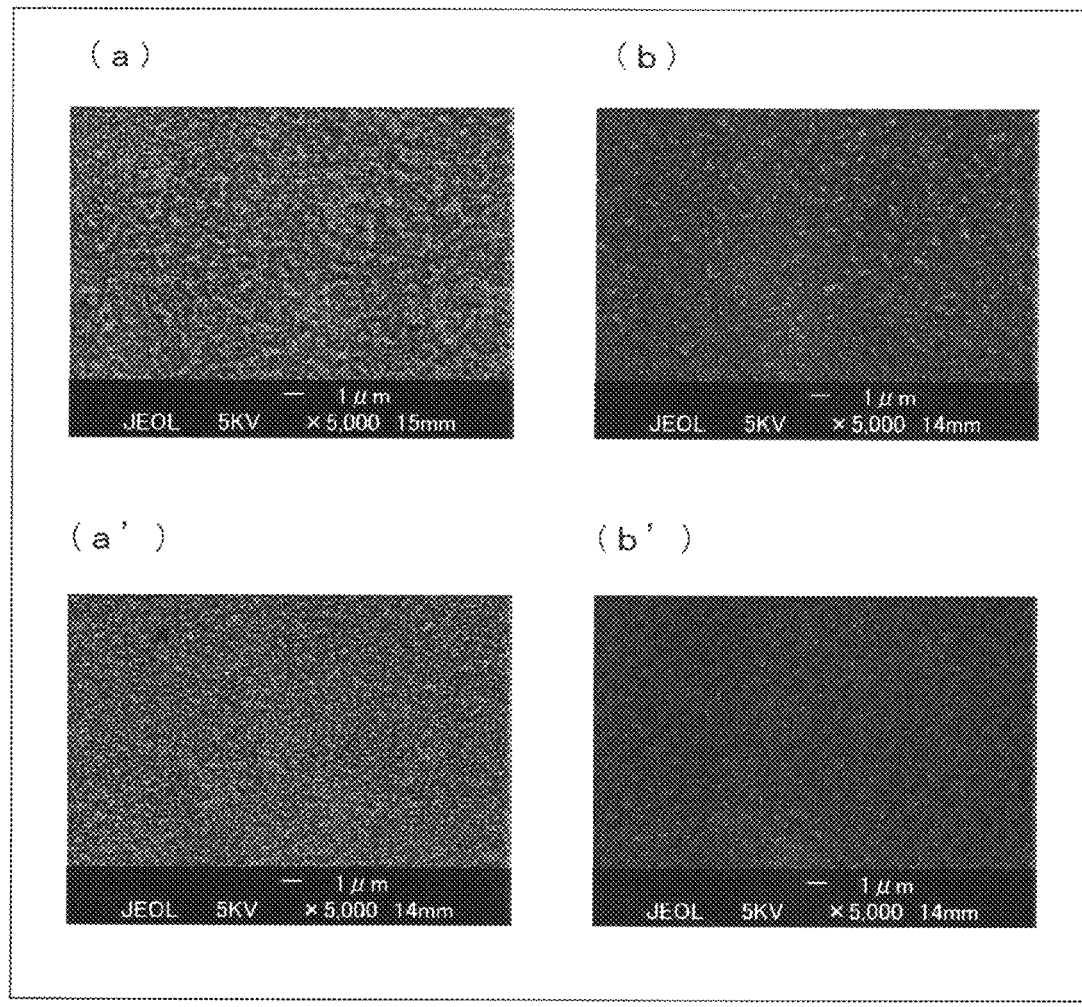
FIG. 14 is a diagram illustrating results of observation of a surface of a Hap complex obtained in Example 14 and a surface of Comparative Example 10 before and after ultrasonic probe treatment; (a) and (b) of FIG. 14 show a result of observation of the surfaces of the hydroxyapatite complexes before the ultrasonic probe treatment and (a') and (b') of FIG. 14 show a result of observation of the surfaces of the hydroxyapatite complexes after the ultrasonic probe treatment.

A comparative hydroxyapatite complex used for comparison was obtained by the same method as in Example 13 except that the graft polymerization was not performed and a substrate was directly coated with the Hap. This Hap complex is referred to as "Comparative Example 10". FIG. 14 shows a result of the comparison.

FIG. 14 is a diagram illustrating results of observation of a surface of the Hap complex obtained in the present example and a surface of Comparative Example 10 before and after ultrasonic probe treatment; (a) and (b) of FIG. 14 show a result of observation of the surfaces of the hydroxyapatite complexes before the ultrasonic probe treatment and (a') and (b') of FIG. 14 show a result of observation of the surfaces of the hydroxyapatite complexes after the ultrasonic probe treatment. It should be noted that (a) and (a') of FIG. 14 show the results of observation of the Hap complex obtained in the present example whereas (b) and (b') of FIG. 14 show the results of observation of the Hap complex of Comparative Example 11.

As shown in FIG. 14, the Hap coating of the Hap complex of Example 14 was preferable before the ultrasonic probe treatment, whereas an amount of Hap coating in the case of Comparative Example 10 was small. Further, it was observed that the Hap particles were peeled off after the ultrasonic probe treatment in the case of Comparative Example 10; however, in the Hap complex of Example 14, it was not observed that the Hap particles were peeled off.

This showed that, in the case where polystyrene is used as the substrate, the Hap coating becomes favorable as in Example 13 when the substrate is treated with the use of acrylic acid rather than directly coated with the Hap. This also showed that because the Hap adheres to the substrate not physically but chemically as a result of the treatment with use of acrylic acid, the Hap particles can be prevented from being peeled off even in a case where the ultrasonic probe treatment is performed on the substrate.

As described above, a method of the present invention for producing a calcium phosphate complex including a substrate and calcium phosphate bonded to a surface of the substrate, the method includes the steps of: (a) treating the surface of the substrate; and (b) bonding the calcium phosphate onto the surface of the substrate after the step (a), the step (a) being the step of placing the surface of the substrate in contact with ozone water. Therefore, the method of the present invention makes it possible to bond calcium phosphate and the substrate at a high bonding strength and at a high coverage. In addition, the method of the present invention can provide an easy method for producing a calcium phosphate complex.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

The method of the present invention for producing a calcium phosphate complex makes it possible to easily produce a calcium phosphate complex including a substrate and calcium phosphate which is bonded to the substrate at a high bonding strength and at a high coverage. Accordingly, the method can be suitably applied to production of a percutaneous device such as a catheter. Therefore, the method of the present invention is suitably utilized in medical instrument industry.

The invention claimed is:

1. A method for producing a calcium phosphate complex including a substrate and calcium phosphate bonded to a surface of the substrate, the method comprising the steps of:
   (a) treating the surface of the substrate; and
   (b) bonding the calcium phosphate onto the surface of the substrate after the step (a),
   the step (a) being the step of placing the surface of the substrate in contact with ozone water,
   the ozone water having an ozone concentration of 27 ppm,
   wherein the substrate is silk,
   the step (b) being the step of bonding the calcium phosphate to a functional group after introducing the functional group onto the surface of the substrate by using a silane coupling agent.

2. A method for producing a calcium phosphate complex including a substrate and calcium phosphate bonded to a surface of the substrate, the method comprising the steps of:
   (a) treating the surface of the substrate; and
   (b) bonding the calcium phosphate onto the surface of the substrate after the step (a),
   the step (a) being the step of placing the surface of the substrate in contact with ozone water,
   the ozone water having an ozone concentration of 27 ppm,
   the surface of the substrate being kept in contact with the ozone water for a time in a range of 5 minutes or more to 30 minutes or less,
   wherein the substrate is silk,
   the step (b) being the step of bonding the calcium phosphate to a functional group after introducing the functional group onto the surface of the substrate by using a silane coupling agent.

3. A method for producing a calcium phosphate complex including a substrate and calcium phosphate bonded to a surface of the substrate, the method comprising the steps of:
   (a) treating the surface of the substrate; and
   (b) bonding the calcium phosphate onto the surface of the substrate after the step (a),
   the step (a) being the step of placing the surface of the substrate in contact with ozone water,
   the ozone water having an ozone concentration of 27 ppm,
   the surface of the substrate being placed in contact with the ozone water at a temperature in a range of 20° C. or more to 60° C. or less,
   wherein the substrate is silk,
   the step (b) being the step of bonding the calcium phosphate to a functional group after introducing the functional group onto the surface of the substrate by using a silane coupling agent.

4. A method for producing a calcium phosphate complex including a substrate and calcium phosphate bonded to a surface of the substrate, the method comprising the steps of:
   (a) treating the surface of the substrate; and
   (b) bonding the calcium phosphate onto the surface of the substrate after the step (a),
   the step (a) being the step of placing the surface of the substrate in contact with ozone water,
   the ozone water having an ozone concentration of 27 ppm,
   the surface of the substrate being placed in contact with the ozone water at a temperature in a range of 20° C. or more to 60° C. or less,
   the surface of the substrate being kept in contact with the ozone water for a time in a range of 5 minutes or more to 30 minutes or less,
   wherein the substrate is silk,
   the step (b) being the step of bonding the calcium phosphate to a functional group after introducing the functional group onto the surface of the substrate by using a silane coupling agent.

* * * * *